United States Patent
Dormer et al.

(10) Patent No.: US 6,936,618 B2
(45) Date of Patent: *Aug. 30, 2005

(54) CYSTIC FIBROSIS MEDICAMENTS

(75) Inventors: Robert Leslie Dormer, Cardiff (GB); Margaret Ann McPherson, Cardiff (GB)

(73) Assignee: University of Wales College of Medicine, Cardiff (GB)

( * ) Notice: Subject to any disclaimer, the term of this patent is extended or adjusted under 35 U.S.C. 154(b) by 19 days.

This patent is subject to a terminal disclaimer.

(21) Appl. No.: 10/394,220

(22) Filed: Mar. 24, 2003

(65) Prior Publication Data

US 2003/0229117 A1 Dec. 11, 2003

Related U.S. Application Data

(62) Division of application No. 09/959,122, filed as application No. PCT/GB00/01564 on Apr. 20, 2000, now Pat. No. 6,599,907.

(30) Foreign Application Priority Data

Apr. 22, 1999 (GB) .............................................. 9909135

(51) Int. Cl.$^7$ ............................................. A61K 31/522
(52) U.S. Cl. ................. 514/263.3; 514/263.1; 514/263.2
(58) Field of Search ........................... 514/263.1, 263.2, 514/263.3, 262.1, 258.1, 261.1, 264.1, 265.1

(56) References Cited

U.S. PATENT DOCUMENTS 5,602,110 A  2/1997  Drumm et al.
5,728,705 A  3/1998  Lawson et al.

OTHER PUBLICATIONS

McPherson et al. "A cyclic nucleotide PDE5 inhibitor corrects defective mucin secretion in submandibular cells containing antibody directed against the cystic fibrosis transmembrane conductance regulator protein," FEBS LETT. vol. 464, pp. 48–52, 1999.

*Primary Examiner*—Dwayne C. Jones
(74) *Attorney, Agent, or Firm*—Young & Thompson

(57) ABSTRACT

The use of a type V cyclic nucleotide phosphodiesterase inhibitor for the preparation of a medicament for the treatment of cystic fibrosis.

5 Claims, 1 Drawing Sheet

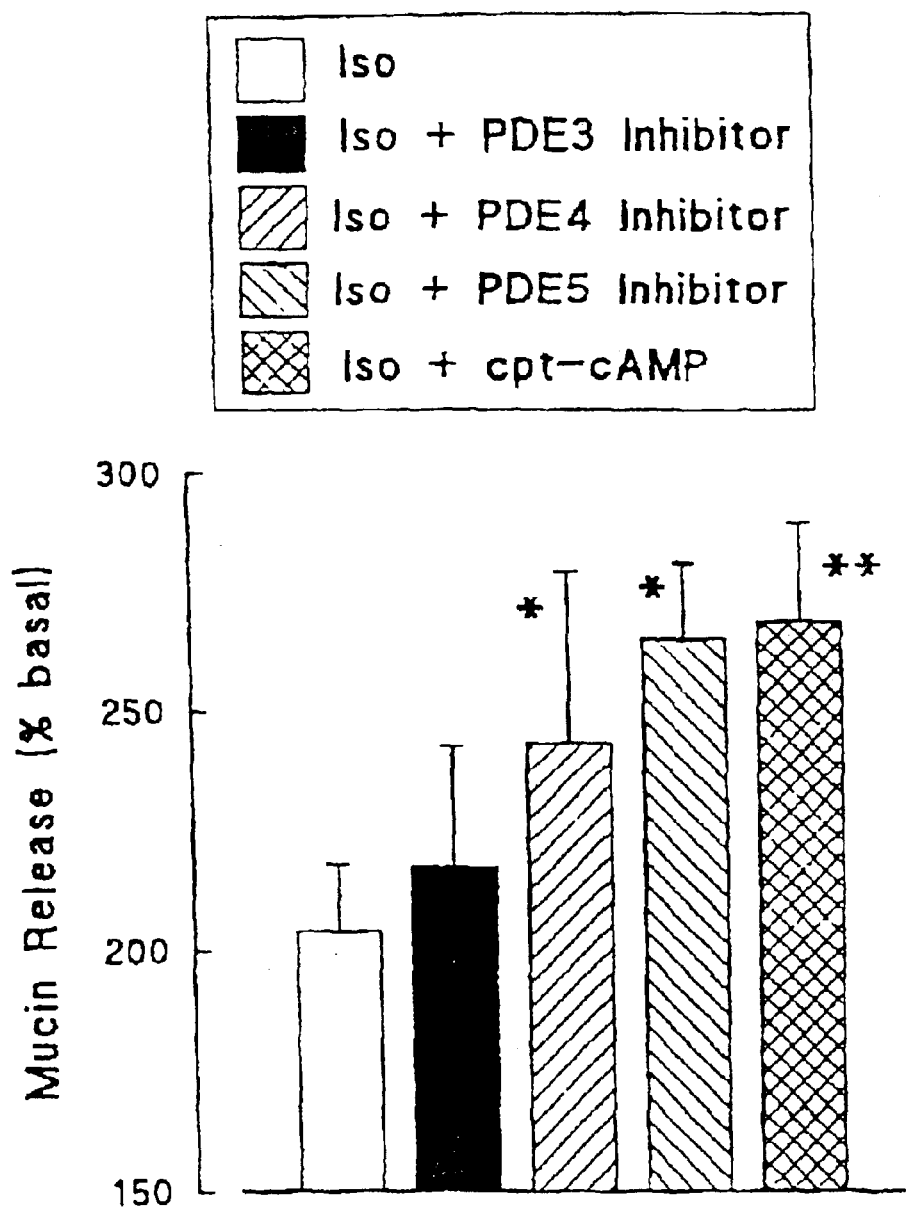

CYSTIC FIBROSIS MEDICAMENTS

The present invention relates to the use of a type V cyclic nucleotide phosphodiesterase inhibitor for the preparation of a medicament for the treatment of cystic fibrosis. In particular, it relates to the use of specific inhibitors for the preparation of a medicament for the treatment of cystic fibrosis.

Cystic fibrosis (CF) is an autosomal recessive disease characterised by disturbances in ion transport and viscous epithelial mucous secretions. The CF gene protein, CFTR acts as a Cl-channel and is also a key regulator of protein secretion.

CF is caused by mutations in the CF gene, which includes the cystic fibrosis transmembrane conductance regulator protein (CFTR).

WO-A-98/19679 discloses the use of 8-cyclopentyl theophylline (CPT) for the preparation of medicaments for the treatment of cystic fibrosis.

It has now been found that a type V cyclic nucleotide phosphodiesterase (PDE) inhibitor corrects the defective mucin secretory response to the β-agonis isoproterenol in CFTR antibody inhibited submandibular acini. Thus, a type V PDE inhibitor corrects defective CFTR function leading to rational drug treatment for cystic fibrosis.

A type V PDE inhibitor is as effective as IBMX or cpt-cyclic AMP. However, in contrast to IBMX and a selective type IV PDE inhibitor, the type V inhibitor has no effect on cyclic AMP levels and does not stimulate wild type mucin secretion. The data show that correction does not correlate with increase in cyclic nucleotide levels.

According to a first aspect of the present invention, there is provided the use of a type V cyclic nucleotide phosphodiesterase inhibitor in the preparation of a medicament for the treatment of cystic fibrosis.

Suitable type V cyclic nucleotide PDE inhibitors for use in the invention include those described in EP 347146, EP 351058, EP 352960 and in J. Med. Chem., 1993, 36 (10), 1387–92.

The type V cyclic nucleotide PDE inhibitor is preferably a selective type V cyclic nucleotide PDE inhibitor.

Compounds can be identified as type V cyclic nucleotide PDE inhibitors using methods known to those skilled in the art, for example as described in EP 293063.

According to a second aspect of the present invention, there is provided the use of a compound of formula (I),

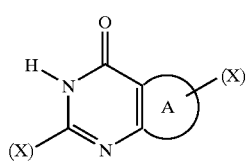
(I)

wherein A is a five or six-membered ring containing one or more N atoms,

X is a substituent of formula (II),

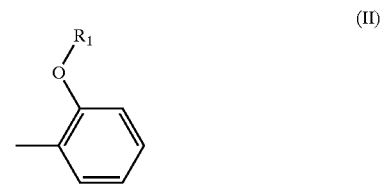
(II)

wherein $R_1$, represents $C_{1-4}$ alkyl, and
X is positioned at either or both of the 2-position and/or the 8-position in (I), in the preparation of a medicament for the treatment of cystic fibrosis.

Preferably, ring A in the compound of formula (I) is of the formula:

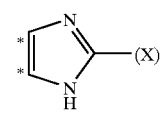

wherein * denotes the points of attachment of the ring, more preferably ring A is of the formula:

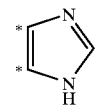

Alternatively, ring A may be of the formula:

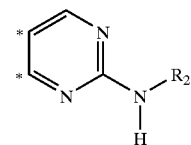

wherein $R_2$ represents hydrogen or $C_{1-4}$ alkyl and * denotes the points of attachment of the ring.

Alternatively, ring A may be of the formula:

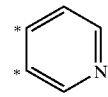

wherein * denotes the points of attachment of the ring.

In particular, the substituent X is preferably only positioned at the 2-position, i.e. on the 4-pyrimidone ring, in the compounds of formula (I).

According to a further aspect of the present invention, there is provided the use of a compound of formula (III):

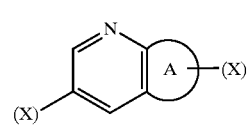
(III)

wherein A is a five- or six-membered ring containing one or more N atoms,
X is a substituent of formula (II):

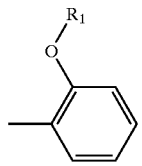

(II)

wherein $R_1$ represents $C_{1-4}$ alkyl, and
X is positioned at either or both of the 2-position and/or the 8-position, in the preparation of a medicament for the treatment of cystic fibrosis.

Preferably, ring A of compound (III) has the following formula:

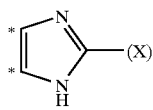

wherein * denotes the points of attachment of the ring.

In particular, the substituent X is preferably only positioned at the 8-position, i.e. on ring A, in the compounds of formula (III).

The compounds of formulae (I) and (III) may be prepared as described in EP 347146, EP 351058, EP 352960 and J. Med. Chem., 1993, 36 (10), 1387–92.

In order to use type V cyclic nucleotide PDE inhibitors in therapy, they will normally be formulated into a pharmaceutical composition in accordance with standard pharmaceutical practice.

The type V cyclic nucleotide PDE inhibitors may be presented in a form suitable for oral administration in a pharmaceutical vehicle convenient for that administrative route. Thus, for example, the medicament may be presented as tablets, capsules, ingestible liquid or a powder preparation. Such formulations can include pharmaceutically acceptable carriers known to those skilled in the art. Formulations suitable for oral administration further include lozenges, pastilles, aerosols and mouthwashes. The type V cyclic nucleotide PDE inhibitors may also be administered by inhalation, that is by intranasal and oral inhalation administration. Formulations suitable for inhalation include powders where the carrier is a solid, and where the carrier is a liquid, the formulation can be administered as a nasal spray or aerosol, or as drops for example.

In yet another alternative, the type V cyclic nucleotide PDE inhibitors may be presented in a formulation suitable for parenteral intravenous administration, such as aqueous or non-aqueous sterile injectable solutions. Such solutions may contain antioxidants, buffers, bacteriostats and solutes which render the formulation isotonic with the blood of the intended recipient. Alternatively, the formulation for parenteral administration may be presented as an aqueous or non-aqueous sterile suspension which may include suspending agents and thickening agents.

It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests.

According to a further aspect of the present invention, there is provided a method of treating cystic fibrosis comprising administering a type V cyclic nucleotide phosphodiesterase inhibitor to a patient in need thereof. The type V cyclic nucleotide PDE inhibitor may be a compound of formula (I) or formula (III) as mentioned above.

All publications, including but not limited to patents and patent applications, cited in this specification are herein incorporated by reference as if each individual publication were specifically and individually indicated to be incorporated by reference herein as though fully set forth.

Whilst the invention has been described above, it extends to any inventive combination of the features set out above or in the following description. The invention will now be described, by way of example, with reference to the following drawing and examples.

FIG. 1 shows the correction of CFTR antibody-inhibited β-adrenergic stimulation of mucin secretion by PDE inhibitors.

EXAMPLES

Methods

Production of Anti-peptide CFTR Antibodies

A peptide consisting of 14 amino acids (524–537), residing in the first nucleotide binding domain (NBD) region of CFTR, was synthesized and coupled to keyhole limpet haemocyanin (KLH) (10 mg peptide/8 mg KLH) by Cambridge Research Biochemicals Ltd, Northwich, Cheshire. The peptide sequence was searched for in the Swissprot database (release of 21 Mar. 1992, Daresbury Lab., Seqnet facility) and only CFTR was found to contain a perfect match. Antisera were prepared as described (Lloyd Mills et al. (1992) Biochem. Biophys. Res. Commun., 188, 1146–1152 and Pereira et al, (1998) Brit. J. Pharmacol., 125, 697–704) and affinity-purified using KLH or peptide coupled to CH-Sepharose 4B (Pharmacia). The IgG content of antisera was estimated either following precipitation with 24% $Na_2SO_4$ for 2 h at room temp. (KLH-Sepharose purified) or directly (peptide-Sepharose purified), using the BioRad protein assay kit. Isolation of rat submandibular acini, incorporation of antibodies into intact acini and measurement of mucin secretion Procedures were carried out as previously described (Lloyd Mills et al, Biochem. Biophys. Res. Commun., 1992, 188, 1146–1152, and Pereira et al, Br. J. Pharmacol., 1998, 125, 697–681). Briefly, acini were pulse-chase labelled with [$^3$H]-glucosamine and suspended in TES-buffered saline (10 mM TES (N-Tris-(hydroxymethyl)-methyl-2-aminoethanesulphonic acid), pH 7.4 containing 143 mM NaCl, 4.7 mM KCl, 1.1 mM $MgCl_2$, 1 mg/ml bovine serum albumin BSA). An equal volume of either 10 mM TES, pH 7.4 (swollen) or TES-buffered saline (unswollen), each containing 5 mM ATP and antibody (1 mg/ml) was added for 1.5 min at room temperature, followed by washing and resuspension in Krebs-Henseleit bicarbonate (KHB) buffer containing 20 mg/ml BSA. Following a 15 min recovery incubation at 37° C. in KHB buffer, acini were washed and incubated under experimental conditions at 37° C. Isoproterenol and 3-isobutyl-1-methylxanthine (IBMX) were dissolved directly into KHB medium at the concentrations used; the selective type III–V PDE inhibitors were dissolved initially in DMSO and diluted to give a final concentration of <1% DMSO in the incubations. An equivalent amount of DMSO was added to control incubations. Type V PDE inhibitor was the least soluble, hence a concentration of 0.2 mM, rather than 1 mM was used. [$^3$H]-labelled mucins, released into the medium at zero time and after 30 min, were acid-precipitated and their radioactivity measured as described by Lloyd Mills et al, Biochem. Biophys. Res. Commun., 1992, 188, 1146–1152, and Pereira et al, Br. J. Pharmacol., 1998, 125, 697–681. Protein content of cell pellets was determined using the BioRad protein assay kit and mucin release over 30 min expressed as dpm/mg protein or as % basal secretion to take account of variation in unstimulated mucin release between experiments.

Measurement of Cyclic AMP and Cyclic GMP Content

Aliquots of acini suspensions (0.5 ml) were added to an equal volume of ice cold trichloroacetic acid (20%), extracted and assayed using specific radio immunoassay kits for cyclic AMP and cyclic GMP (Amersham), as described by Lloyd Mills et al, Biochem. Biophys. Res. Commun., 1992, 188, 1146–1152.

Results

The mechanism of action of IBMX in correcting defective CFTR function was investigated using (R,S)-4,5-dihydro-6-[4-(1,4-dihydro-4-oxopyridin-1-yl) phenyl]-5-methyl-3 (2H)-pyridazinone a selective type III (cyclic AMP activated, cyclic GMP inhibited) PDE inhibitor, 4-(3-cyclopentyloxy-4-methoxyphenyl)-2-pyrrolidinone a type IV (cyclic AMP activated) PDE inhibitor, and 1,7-dihydro-2-(2-propoxyphenyl)-6H-purin-6-one a type V (cyclic GMP activated) PDE inhibitors. The structure of these compounds is shown below:

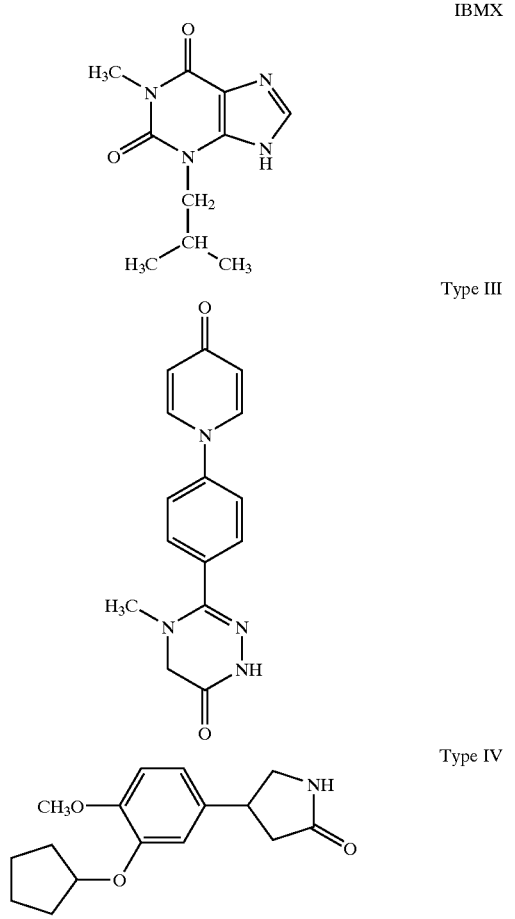

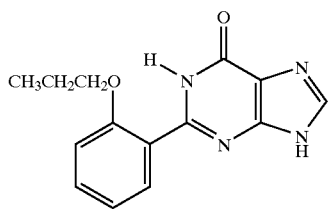

Table 1 shows the actions of maximally effective concentrations of isoproterenol (IP), IBMX and the selective cyclic nucleotide PDE inhibitors on mucin secretion and cyclic AMP rise from rat submandibular acini. Mucin secretion was measured at 30 min; cyclic AMP at 5 min, when maximum stimulation is seen. Isoproterenol and IBMX were the most potent stimulators of mucin secretion, giving a similar maximum stimulation; however isoproterenol increased cyclic AMP to a much greater extent than IBMX. The type IV PDE inhibitor gave the same cyclic AMP rise as isoproterenol but was much less effective in stimulating mucin secretion. The type III and type V PDE inhibitors did not significantly increase cyclic AMP or mucin secretion. The data indicate a lack of correlation between magnitude of increase in cyclic AMP and stimulation of mucin secretion and are in accord with previous results (Bradbury et al, Biochem. Biophys. Res. Commun., 1998, 161, 661–671 and Lloyd Mills et al, FEBS Lett., 1991, 298, 141–144) showing dissociation of cyclic AMP rise and mucin secretion which suggest that cyclic AMP is not the sole intracellular messenger involved.

FIG. 1 shows the actions of the selective cyclic nucleotide PDE inhibitors on the defective isoproterenol-stimulated mucin secretion in rat submandibular cells containing CFTR antibody (approx. 1 mg IgG/ml) which had been introduced as described in the Methods by hypotonic swelling. The actions of the PDE inhibitors in increasing the CFTR antibody-inhibited response was compared to that of cpt-cyclic AMP, which has been shown to restore secretory responsiveness to the same extent as IBMX (ImM), giving approx. 75% of the secretion response seen in cells containing an equivalent amount of non-immune IgG. The data show that type IV and type V PDE inhibitors are as effective as cpt-cAMP in correcting the defective B-adrenergic secretory response, whereas the type III PDE inhibitor was ineffective. Referring to FIG. 1, rat submandibular acini were pulse-chase labelled with $^3$H-glucosamine and swollen in the presence of CFTR antibody as described in the Methods. Mucin secretion in the presence of isoproterenol, (Iso-10 μM) and PDE inhibitors (PDE I Types III and IV at 1 mM; Type V at 0.2 mM) or cpt-cyclic AMP (1 mM) as shown, was measured after 30 min. Results are mean±SEM for at least 4 experiments and are expressed as % basal. *, $p<0.05$, **, $p<0.01$ for difference from secretion in the presence of isoproterenol alone as assessed by Student's t-test.

IBMX potentiates the cyclic AMP rise in the presence of isoproterenol, giving excessive increase in cyclic AMP above the levels induced physiologically by B-adrenergic stimulation, although it does not increase mucin secretion above the maximum induced by isoproterenol. The actions of the selective cyclic nucleotide PDE inhibitors on isoproterenol stimulated mucin secretion and cyclic AMP rise have been compared to that of IBMX as shown in Table 2. Previous results have shown that the cyclic AMP response of non-swollen cells or cells swollen in the presence of either non-immune IgG or CFTR antibody are not different. It is noteworthy that like IBMX, none of the selective PDE inhibitors significantly increased mucin secretion above the maximum response induced by isoproterenol alone, even through IBMX, type III and type IV inhibitors massively potentiated the isoproterenol induced cyclic AMP rise. Table 2 also shows that the type III PDE inhibitor was as effective as IBMX in potentiating the cyclic AMP rise induced by isoproterenol alone and the type IV inhibitor was even more effective. However, the Type V PDE inhibitor did not potentiate the isoproterenol induced cyclic AMP response. This raised the question as to the role of cyclic GMP in the correction of CFTR function by the Type V PDE inhibitor. Table 3 shows that isoproterenol alone caused a very small increase in cyclic GMP, which was further increased in the presence of IBMX or the selective Type V PDE inhibitor. Type III and type IV PDE inhibitors did not change cyclic GMP in the presence or absence of isoproterenol (Table 3).

Further selective type V PDE inhibitors as shown in Table 4 were also tested for their actions in correcting CFTR function. Table 5 shows their potency of correction compared to 1 mM cpt-cyclic AMP.

The mechanism of action of the selective PDE inhibitors in correcting defective CFTR function did not correlate with their ability to stimulate mucin secretion nor to cause excessive increase in cyclic AMP. Thus, the type IV PDE inhibitor stimulated mucin secretion, gave excessive increase in cyclic AMP and corrected CFTR activity whereas the type III PDE inhibitor did not stimulate mucin secretion, gave excessive increase in cyclic AMP but did not correct CFTR activity. The type V PDE inhibitor corrected CFTR activity without stimulating mucin secretion or cyclic AMP.

TABLE 1

Actions of cyclic nucleotide PDE inhibitors on mucin secretion and cyclic AMP levels in rat submandibular acini.

| Additions | Mucin Secretion (% basal) | Cyclic AMP (pmol/mg protein) |
|---|---|---|
| No addition | 100 ± 9 | 9.4 ± 2.7 |
| Isoproterenol (10 μM) | **619 ± 101 | ††160.3 ± 23.1 |
| IBMX (1 mM) | **578 ± 84 | †27.9 ± 4.9 |
| Type III (1 mM) | 139 ± 42 | 11.8 ± 1.7 |
| Type IV (1 mM) | *191 ± 20 | †168 ± 36.6 |
| Type V (0.2 mM) | 122 ± 35 | 4.9 ± 0.6 |

Mucin release was measured at 30 min and cyclic AMP at 5 min as described in the Methods, in the presence or absence of agonists. Mucin release is expressed as % basal, due to the variation in basal between experiments. Results are means ± SEM for at least three experiments. Significance of differences was assessed by Students t-test:
*p < 0.002;
**p < 0.001 for difference from basal mucin secretion;
†p < 0.05;
††p < 0.01 for difference from basal cyclic AMP.

TABLE 2

Actions of cyclic nucleotide PDE inhibitors on isoproterenol-stimulated mucin secretion and cyclic AMP levels in rat submandibular acini.

| | Mucin Secretion (% basal) | Cyclic AMP (pmol/mg protein) |
|---|---|---|
| No addition | 100 ± 7 (6) | 7.9 ± 1.9 (5) |
| Isoproterenol (10 μM) | 785 ± 212 (6) | 373.0 ± 84.0 (6) |
| Isoproterenol (10 μM) + IBMX (1 mM) | 924 ± 290 (6) | *1252.9 ± 129.6 (6) |
| Isoproterenol (10 μM) + Type III (1 mM) | 692 ± 238 (6) | *1009.6 ± 91.5 (6) |
| Isoproterenol (10 μM) + Type IV (1 mM) | 708 ± 220 (6) | **1908.7 ± 150.8 (6) |
| Isoproterenol (10 μM) + Type V (0.2 mM) | 755 ± 243 (6) | 375.5 ± 95.8 (6) |

Mucin secretion was measured at 30 min and cyclic AMP at 5 min as described in the Methods, under the conditions shown. Mucin secretion is expressed as % basal, due to the variation between experiments. Numbers in parentheses represent the number of observations. Significance of difference was assessed by Students unpaired t-test.
*p < 0.001;
**p < 0.0001 for difference from stimulation by isoproterenol alone.

TABLE 3

Actions of cyclic nucleotide PDE inhibitors on cyclic GMP levels in the presence or absence of isoproterenol.

| | Cyclic GMP (fmol/mg protein) | |
|---|---|---|
| | No Isoproterenol | +Isoproterenol (10 μM) |
| No addition | 39.2 ± 1.0 (6) | 45.2 ± 1.6 (4) |
| IBMX (1 mM) | 48.1 ± 5.2 (8) | **55.6 ± 1.6 (8) |
| Type III (1 mM) | 39.3 ± 2.4 (3) | 47.0 ± 1.8 (4) |
| Type IV (1 mM) | 40.1 ± 1.5 (3) | 45.2 ± 2.0 (4) |
| Type V (0.2 mM) | *47.3 ± 2.5 (5) | **64.3 ± 3.6 (5) |

Cyclic GMP levels were measured as described in the Methods following 5 min incubation under the conditions shown. PDE inhibitor concentrations used were 1 mM for IBMX, Types III and IV and 0.2 mM for Type V. Results are mean ± SEM for the number of experiments shown in parentheses. Significance of difference was assessed by Students t-test.
*p < 0.02 for difference from basal (no isoproterenol); all conditions in the presence of isoproterenol were significantly different from basal (p < 0.05);
**p < 0.005 for difference from stimulation by isoproterenol alone.

TABLE 4

| COMPOUND | STRUCTURE | PDE V IC$_{50}$ (μm) |
|---|---|---|
| a) | 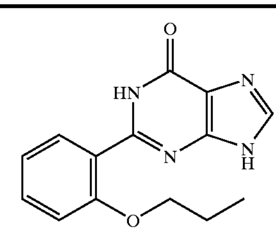 | 0.96 |
| b) | 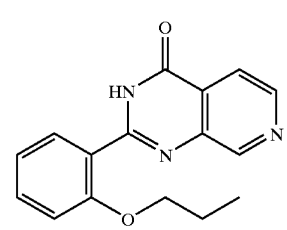 | 0.55 |

TABLE 4-continued

| COMPOUND | STRUCTURE | PDE V IC$_{50}$ ($\mu$m) |
|---|---|---|
| c) | 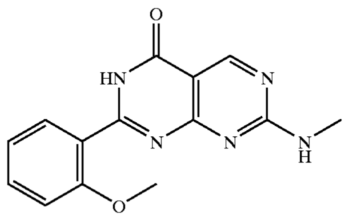 | 22 |
| d) | 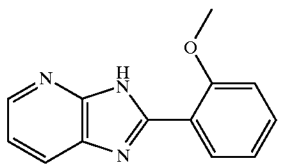 | 34 |
| e) | 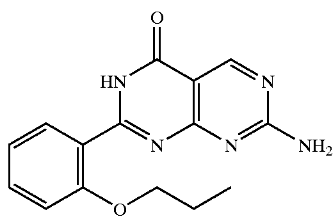 | 0.65 |
| f) | 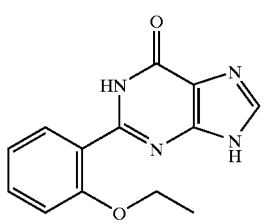 | 4.5 |
| g) | 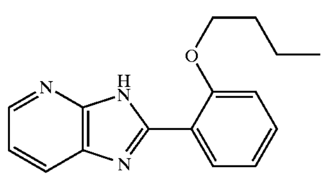 | 0.75 |
| h) | 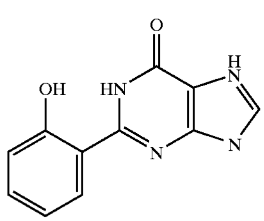 | 48 |
| i) | 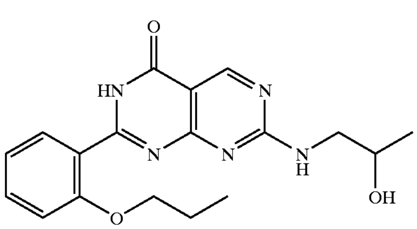 | 0.2 |
| j) | 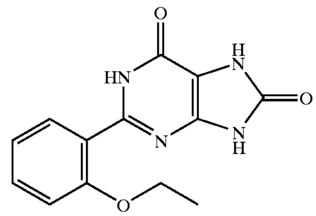 | 1.3 |

TABLE 5

Actions of compounds on correction of CFTR function, wild type mucin secretion and cyclic AMP and cyclic GMP levels.

| Compound | Degree of Correction compared to 1 mM cAMP % cAMP response | Mucin secretion % basal | cyclic AMP % basal | cyclic GMP % basal |
|---|---|---|---|---|
| a) | 100* | 120 | 100 | 140 |
| b) | 100* | 180* | 600* | 130 |
| c) | 100* | 160* | 250* | 90 |
| d) | 100* | 200* | 600* | 90 |
| e) | 50 | 170* | 350* | 130 |
| f) | 33 | 160* | 100 | 110 |
| g) | 20 | 200* | 160* | 110 |
| h) | 0 | 180* | 100 | 110 |
| i) | 0 | 170* | 100 | 90 |
| j) | 0 | 160* | 100 | 140* |

*indicates significant difference from basal.

The results show that a selective Type V cyclic nucleotide PDE inhibitor corrected defective β-adrenergic stimulation of mucin secretion induced by CFTR antibody. The Type V PDE inhibitor did not increase cyclic AMP levels, nor did it potentiate isoproterenol induced cyclic AMP rise. The data show that the CFTR mucin secretion defect can be corrected without increase in cyclic AMP and imply specificity in correction of the CFTR defect.

A lack of correlation between magnitude of increase in cyclic AMP and stimulation of mucin secretion in submandibular cells was observed in that IP and IBMX maximally stimulated mucin secretion, but IBMX gave a much lower cAMP response and the type IV PDE inhibitor increased cyclic AMP to the same extent as IP, but gave much less stimulated mucin secretion. The data are in accord with previous results showing dissociation between cAMP rise and mucin secretion, indicating that this is not the sole intracellular messenger involved. Stimulation of wild type mucin secretion was not a prerequisite for correction of CFTR activity, as shown by the lack of stimulation of mucin secretion by the active type V PDE inhibitor.

It is not clear whether the non selective PDE inhibitor IBMX and the type IV PDE inhibitor, which increase cyclic AMP and potentiate IP-induced cyclic AMP rise, correct defective CFTR function by an excessive increase in cyclic AMP. Results using the type III PDE inhibitor, showing the same isoproterenol induced cyclic AMP rise as IBMX but no restoration of CFTR activity, suggest that excessive increase in cyclic AMP alone is not sufficient to correct defective CFTR function.

The finding that a Type V PDE inhibitor corrected CFTR function, raised the question as to whether cyclic GMP was involved. The predominant PDE in submandibular tissues is the type IV enzyme. In submandibular acini, isoproterenol increases cyclic GMP to a small extent, which is further increased in the presence of IBMX or the type V PDE inhibitor. Thus the mechanism of correction by the type V PDE inhibitor may be mediated by cyclic GMP, but other actions such as direct interaction with CFTR are also possible, and the applicant is not to be bound thereby.

In accord with these findings, other structurally related analogues of the selective type V PDE inhibitor are active in correcting CFTR function (Table 5). Whilst the applicant is not to be bound hereby, these compounds could be directly interacting with CFTR.

What is claimed is:

1. A method of treating cystic fibrosis in a patient, comprising:

administering to said patient an effective amount of a type V cyclic nucleotide phosphodiesterase inhibitor, wherein said inhibitor is a compound of formula (I):

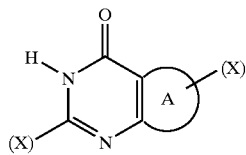

wherein A is a five- or six-membered ring containing one or more N atoms, X is a substituent of formula (II):

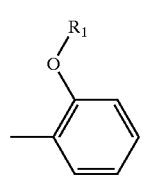

or a variant of formula II having a further substituent on the ring, wherein $R_1$ represents $C_{1-4}$ alkyl, and X is positioned at either or both of the 2-position and the 8-position in (I).

2. The method according to claim 1, wherein ring A is of the formula:

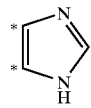

and wherein * denotes the points of attachment of the ring.

3. The method according to claim 1, wherein ring A is of the formula:

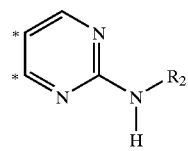

wherein $R_2$ represents hydrogen or $C_{1-4}$ alkyl, and * denotes the point of attachment of the ring.

4. The method according to claim 1, wherein ring A is of the formula:

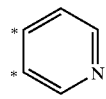

wherein * denotes the points of attachment of the ring.

5. The method according to claim 1, wherein the substituent X is only positioned at the 2-position in (I).

* * * * *